US010874556B2

(12) United States Patent
Lowing

(10) Patent No.: US 10,874,556 B2
(45) Date of Patent: Dec. 29, 2020

(54) HYDROGEL WOUND DRESSING FOR USE WITH SUCTION

(71) Applicant: KCI USA, Inc., San Antonio, TX (US)

(72) Inventor: Paul Howard Lowing, Keighley (GB)

(73) Assignee: KCI USA, Inc., San Antonio, TX (US)

( * ) Notice: Subject to any disclaimer, the term of this patent is extended or adjusted under 35 U.S.C. 154(b) by 576 days.

(21) Appl. No.: 15/808,760

(22) Filed: Nov. 9, 2017

(65) Prior Publication Data

US 2018/0064581 A1    Mar. 8, 2018

Related U.S. Application Data

(63) Continuation of application No. 14/663,203, filed on Mar. 19, 2015, now Pat. No. 9,839,559, which is a (Continued)

(30) Foreign Application Priority Data

Jun. 10, 2009    (GB) .................................. 0910022.3

(51) Int. Cl.
*A61F 13/00*        (2006.01)
*A61F 13/02*        (2006.01)
(Continued)

(52) U.S. Cl.
CPC ........ *A61F 13/00068* (2013.01); *A61F 13/00* (2013.01); *A61F 13/00012* (2013.01);
(Continued)

(58) Field of Classification Search
CPC ................ A61F 13/00; A61F 13/00017; A61F 13/00046; A61F 13/00063;
(Continued)

(56) References Cited

U.S. PATENT DOCUMENTS 5,076,265 A    12/1991  Wokalek
5,612,321 A    3/1997   Nguyen
(Continued)

FOREIGN PATENT DOCUMENTS

EP    0 168 174 A1    1/1986
EP    0 620 720 A1    10/1994
(Continued)

OTHER PUBLICATIONS

Campbell, P., "Surgical Wound Case Studies With the Versatile 1 Wound Vacuum System for Negative Pressure Wound Therapy," J Wound Ostomy Continence Nurs. 2006; 33:2-10 (15 pages).
(Continued)

*Primary Examiner* — Benjamin J Klein
(74) *Attorney, Agent, or Firm* — Foley & Lardner LLP

(57) ABSTRACT

A wound dressing comprising: an air-impermeable backing sheet having an aperture for attachment of a suction element; an air-permeable screen layer on a wound facing side of the backing sheet; and a substantially air-impermeable hydrogel layer extending across a wound facing side of said screen layer and joined in substantially airtight fashion to a periphery of said backing sheet around said screen layer. Also provided is a wound treatment system comprising a wound dressing according to the invention and a source of suction in fluid communication with said aperture.

16 Claims, 1 Drawing Sheet

Related U.S. Application Data continuation of application No. 13/377,071, filed as application No. PCT/GB2010/001143 on Aug. 10, 2010, now Pat. No. 8,992,509.

(51) Int. Cl.
*A61M 1/00* (2006.01)
*A61M 35/00* (2006.01)

(52) U.S. Cl.
CPC .. *A61F 13/00017* (2013.01); *A61F 13/00046* (2013.01); *A61F 13/00063* (2013.01); *A61F 13/02* (2013.01); *A61F 13/0209* (2013.01); *A61F 13/0213* (2013.01); *A61F 13/0216* (2013.01); *A61F 13/0226* (2013.01); *A61M 1/009* (2014.02); *A61F 2013/00268* (2013.01); *A61M 1/0088* (2013.01); *A61M 35/00* (2013.01)

(58) Field of Classification Search
CPC .......... A61F 13/00068; A61F 13/00268; A61F 13/02; A61F 13/0209; A61F 13/0213; A61F 13/0216; A61F 13/0226; A61F 2013/00536; A61M 1/00; A61M 1/0088; A61M 1/009; A61M 35/00
See application file for complete search history.

(56) References Cited

U.S. PATENT DOCUMENTS

| | | | |
|---|---|---|---|
| 5,636,643 | A | 6/1997 | Argenta et al. |
| 5,645,081 | A | 7/1997 | Argenta et al. |
| 5,700,476 | A | 12/1997 | Rosenthal et al. |
| 6,110,483 | A | 8/2000 | Whitbourne et al. |
| 7,520,872 | B2 | 4/2009 | Biggie et al. |
| 7,906,585 | B2 | 3/2011 | McIntosh et al. |
| 8,075,503 | B2 | 12/2011 | Jaeb |
| 2005/0137539 | A1 | 6/2005 | Biggie et al. |
| 2006/0189910 | A1 | 8/2006 | Johnson et al. |
| 2007/0225663 | A1* | 9/2007 | Watt .................. A61F 13/0213 604/313 |
| 2008/0082059 | A1 | 4/2008 | Fink et al. |
| 2008/0215020 | A1 | 9/2008 | Reeves et al. |
| 2009/0227969 | A1 | 9/2009 | Jaeb et al. |
| 2009/0299251 | A1 | 12/2009 | Buan |

FOREIGN PATENT DOCUMENTS

| | | |
|---|---|---|
| EP | 0 688 189 A1 | 12/1995 |
| WO | WO-94/20041 A1 | 9/1994 |
| WO | WO-00/07638 A1 | 2/2000 |
| WO | WO-01/89431 A1 | 11/2001 |
| WO | WO-02/060501 A2 | 8/2002 |
| WO | WO-03/086255 A1 | 10/2003 |
| WO | WO-2004/037334 A1 | 5/2004 |
| WO | WO-2004/052415 A1 | 6/2004 |
| WO | WO-2005/123170 A1 | 12/2005 |
| WO | WO-2007/030601 A2 | 3/2007 |
| WO | WO-2008/005532 A2 | 1/2008 |
| WO | WO-2009/066106 A1 | 5/2009 |
| WO | WO-2010/141271 A1 | 12/2010 |

OTHER PUBLICATIONS

Final Office Action on U.S. Appl. No. 13/377,071 dated Jan. 15, 2014 (12 pages).
Final Office Action on U.S. Appl. No. 14/663,203 dated May 19, 2017 (11 pages).
GB Search Report on GB Appln. Ser. No. GB0910022.3 dated Oct. 6, 2009 (1 page).
International Search Report on PCT Appln. Ser. No. PCT/GB2010/001143 dated Jan. 3, 2011 (5 pages).
Moody, A., "Use of a Hydrogel Dressing for Management of a Painful Leg Ulcer," Wound Care, Jun. 2006 (4 pages).
Non-Final Office Action on U.S. Appl. No. 13/377,071 dated Jul. 2, 2013 (12 pages).
Non-Final Office Action on U.S. Appl. No. 14/663,203 dated Sep. 28, 2016 (13 pages).
Notice of Allowance on U.S. Appl. No. 13/377,071 dated Dec. 3, 2014 (9 pages).
Notice of Allowance on U.S. Appl. No. 14/663,203 dated Sep. 12, 2017 (9 pages).
Office Action on EP Appln. Ser. No. 10724890.8 dated Feb. 19, 2014 (19 pages).

\* cited by examiner

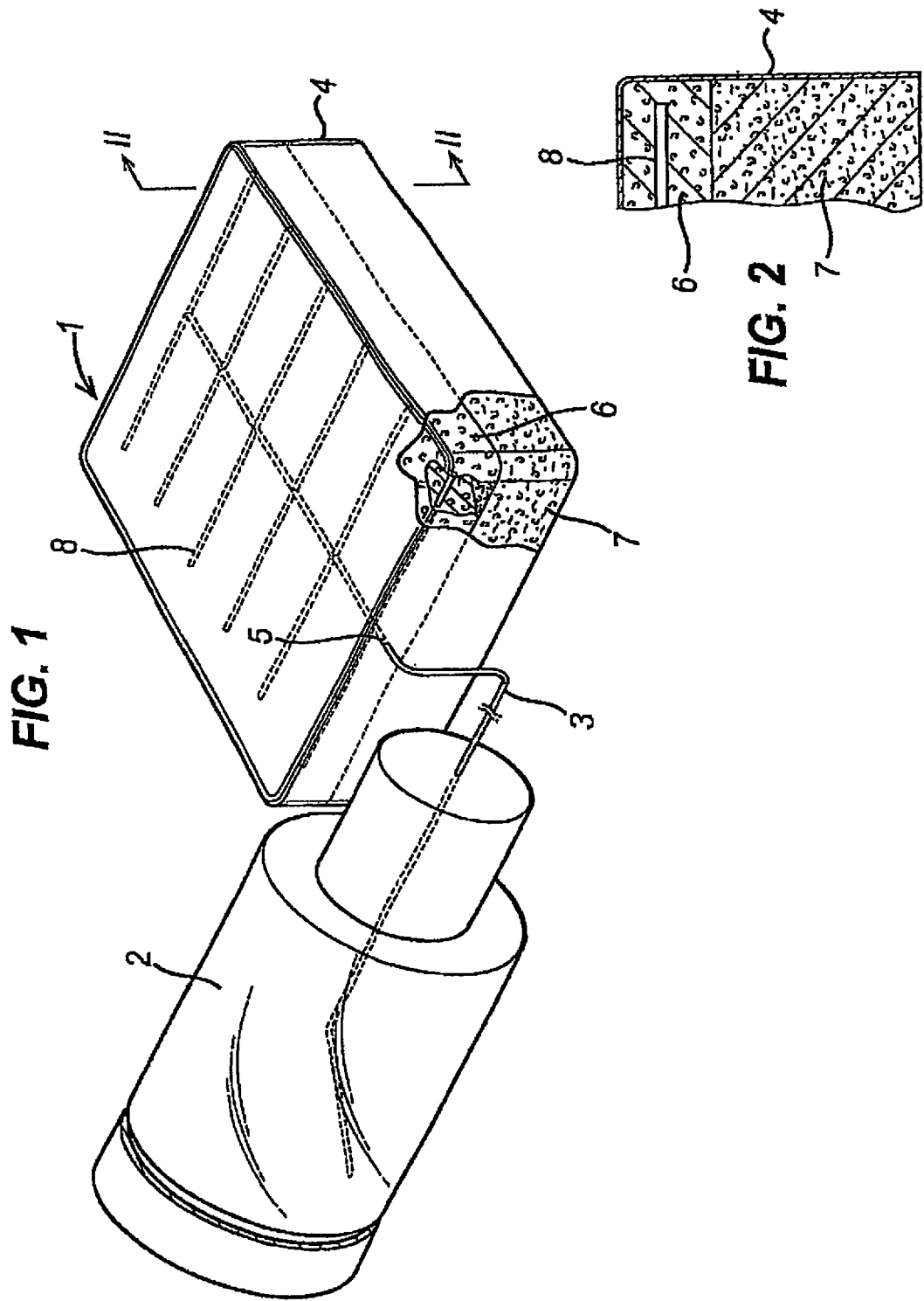

HYDROGEL WOUND DRESSING FOR USE WITH SUCTION

This application is a continuation of U.S. patent application Ser. No. 14/663,203, filed Mar. 19, 2015, which is a continuation of U.S. patent application Ser. No. 13/377,071, filed May 4, 2012, Issued U.S. Pat. No. 8,992,509 on Mar. 31, 2015, which claims priority to U.S. National Stage of International Application No. PCT/GB2010/001143, filed Jun. 10, 2010, which claims priority to Great Britain Patent Application No. 0910022.3, filed Jun. 10, 2009, the contents of which are hereby incorporated by reference in their entirety.

The present invention relates to improved wound dressings incorporating a hydrogel wound contacting layer. The invention also relates to wound treatment systems incorporating such dressings, and to methods of medical treatment with such dressings.

Wound dressings that comprise a continuous, wound-contacting layer of a hydrogel are known. Such dressings exhibit low adhesion to the wound surface, but the rate at which such dressings can absorb liquid from exuding wounds is limited. As a result, liquid may pool underneath these dressings resulting in leakage of liquid from the dressings and maceration of skin around the wound.

U.S. Pat. No. 5,076,265 and WO-A-03086255 describe methods of making apertured hydrogel wound contacting layers that are more liquid-permeable than continuous hydrogel wound contacting layers. However, it will be appreciated that some of the advantages of the continuous hydrogel wound contacting layer are impaired by the presence of apertures.

Vacuum wound dressings, also known as negative pressure wound treatments (NPWT), are known. These dressings apply a reduced pressure continuously to the surface of a wound to promote wound healing.

For example, EP-A-0620720 and EP-A-0688189 describe vacuum treatment for accelerating wound healing. They describe the use of a cover for sealing about the outer perimeter of the wound, under which a vacuum is established to act on the wound surface. This vacuum applied to the wound surface accelerates healing of chronic wounds. A screen of open-cell foam material is provided under the cover to provide the space in which the vacuum is formed and to reduce tissue ingrowth. Sufficient vacuum is applied for a suitable duration to promote tissue migration in order to facilitate the closure of the wound. Suitable pressures above the wound are between about 0.1 and 0.99 atmospheres. The vacuum can be substantially continuous, wherein the pressure is relieved only to change the dressing on the wound. Alternatively, the patent teaches cyclic application of vacuum in alternating periods of application and non-application. In a preferred embodiment, vacuum is applied in 5 minute periods of application and non-application.

WO-A-0189431 describes vacuum wound dressings wherein the screen further comprising a layer of a collagen scaffold material to promote wound healing. The preferred collagen material is small intestine submucosa (SIS).

WO-A-2005123170 describes vacuum wound dressings comprising active screen materials that selectively remove undesirable substances from wound fluid. In certain embodiments, the screen material comprises a gel-forming polymer.

WO-A-2009066106 describes vacuum wound dressings that comprise a reservoir compartment containing a porous material for absorption of wound fluid. In some embodiments the screen is separated from the absorbent layer by a microporous membrane that allows the passage of gas but not liquids.

US-A-20060189910 describes a vacuum wound treatment device having a sponge screen. The wound-facing side of the screen may contain a "growth-enhancing matrix", which may be "a gel-like growth-enhancing matrix". This matrix comprises a cell-growth enhancing substrate that is up to over 90% open space.

US-A-20080215020 describes a vacuum wound dressing having a wound contacting layer which may be gauze impregnated with hydrophilic hydrogel substance. There does not appear to be any disclosure of a continuous hydrogel layer extending across the dressing in air-tight fashion.

WO-A-2008005532 describes wound contacting sheets for vacuum wound dressings. It appears that all of the wound contacting sheets described are air-permeable.

WO-A-2007030601 describes vacuum wound dressings having a wound contacting layer that is said to be typically porous.

In a first aspect, the present invention provides a wound dressing comprising: an air-impermeable backing sheet having an aperture for attachment to a source of suction; an air-permeable screen layer on a wound facing side of the backing sheet; and a substantially air-impermeable hydrogel layer extending across a wound facing side of said screen layer and joined in substantially airtight fashion to a periphery of said backing sheet around said screen layer.

In a second aspect, the present invention provides a wound treatment system comprising a wound dressing according to the invention, and a source of suction in fluid communication with said aperture.

In a further aspect, the present invention provides a method for promoting wound healing comprising the steps of: applying a wound dressing according to the invention to a wound, connecting the aperture to a source of suction, and creating a reduced (i.e. sub-atmospheric) pressure above said hydrogel layer.

The dressings according to the present invention do not normally apply significantly reduced pressure directly to the surface of the wound, and therefore are distinct from the vacuum dressings of the prior art. The dressings of the present invention apply a reduced pressure to the top surface of the wound contacting layer of hydrogel, whereby the pressure differential between the wound facing surface of the hydrogel and the top surface thereof tends to draw liquid through the hydrogel layer, resulting in a hydrogel dressing that is able to absorb liquid from an exuding wound faster than previously known dressings with a continuous hydrogel wound contacting layer.

In certain embodiments of the dressing or system according to the invention, a tube or a coupling is attached to the aperture in the backing sheet for connection to the source of suction. For example, the dressing aperture may be provided with a push, screw, snap, Luer-lock or bayonet-type fitting for attachment of the suction source.

Suitably, the wound dressing of the invention further comprises a suction manifold in fluid communication with the aperture and located inside the screen layer or intermediate the screen layer and the backing sheet. The term "suction manifold" refers to a hollow body having a plurality of apertures for collecting fluid from a plurality of locations under the backing sheet. The manifold may for example comprise a branched tube which may be perforated, an apertured envelope, or a perforated spiral-wound tube. Other suitable suction manifolds are described in WO2004/

037334. The suction manifold may be embedded in the screen layer, but preferably substantially does not contact the hydrogel layer. The suction manifold delivers suction across the dressing and may provide drainage of wound fluid from the screen.

The dressing or system according to the invention may further be provided with a valve for controlling the application of suction through the aperture. In certain embodiments the valve may be closed to maintain a desired atmosphere or pressure in the space above the hydrogel layer, or it may be a one-way or non-return valve to maintain reduced pressure over the hydrogel after removal of the vacuum source.

The backing sheet is formed from a sheet material that is substantially or completely impermeable to air. The backing sheet should suitably be formed from substantially gas-impermeable or semipermeable sheet material in order to be able to maintain a reduced pressure in the space between the hydrogel layer and the backing sheet. Thermoplastic sheet materials of various types are suitable. The backing sheet may suitably be substantially convex, preferably in the shape of a shallow dish. It may be made of a resilient material in order to help maintain reduced pressure above the hydrogel after suction has been applied. The backing sheet may be provided with a layer of a medically acceptable pressure-sensitive adhesive on at least the periphery thereof for attachment of the backing sheet to the skin around the wound to be treated, but this is not essential since the present invention does not seek to maintain a reduced pressure at the wound surface.

The screen provides support for the hydrogel and a reservoir for storage of wound fluid so that it is not necessary continuously to drain fluid from the dressing. Accordingly, the screen is suitably formed from a resilient or rigid, porous water-absorbent material.

Suitable screen materials comprise or consist essentially of open cellular foams formed of a hydrophilic polymeric material, such as polyurethane or polyester. Such foams are advantageous, since they are resilient and therefore they are compressed by the application of vacuum, but do not collapse to the extent that porosity and liquid permeability are lost. Typically the thickness of the screen material is from about 1 mm to about 30 mm, for example from about 5 mm to about 15 mm. Other materials that may be used for the screen include freeze-dried sponges of biopolymers, and nonwoven textile materials. The screen may be made up of a plurality of layers of the same or different materials.

The term "hydrogel" refers to medically acceptable aqueous gel of one or more macromolecular substances that form a gel with water under physiological conditions of temperature and pH. Such hydrogels preferably have the ability to swell and absorb fluid while maintaining a strong integral structure. Preferably, the hydrogel is substantially insoluble in water under physiological conditions, whereby the hydrogel is not washed away by the wound fluid.

Exemplary insoluble hydrogels include certain cross-linked polyacrylate gels, polyacrylamide gels, polyurethane gels, cross-linked biopolymer gels, carboxymethyl cellulose gels, hydroxyethyl cellulose gels, hydroxy propyl methyl cellulose, and gels formed from vinyl alcohols, vinyl esters, vinyl ethers and mixtures thereof. Cross-linked biopolymer gels include calcium alginate gels, cross-linked hyaluronate gels, pectin gels, galactomannan gels, chitosan gels, cross-linked gelatin, and mixtures thereof. Other suitable gels include gels formed from and carboxy vinyl monomers, meth (acrylic) acrylamide, N-vinylpyrrolidone, acylamidopropane sulphonic acid, PLURONIC (Registered Trade Mark) (block polyethylene glycol, block polypropylene glycol) polystyrene-, maleic acid, NN-dimethylacrylamide, diacetone acrylamide, acryloyl morpholine, and mixtures thereof. In certain embodiments, the hydrogel comprises a hydrogel material of the kind described in WO-A-0007638.

The hydrogel may be resorbable, that is to say it may be fully broken down and reabsorbed in vivo in the mammalian body.

The hydrogels may be cross-linked, and the cross-linking may be either covalent or ionic. The hydrogel material may comprise from about 5% to about 99% by weight, for example from about 10% to about 90% by weight of water based on the weight of the hydrogel. The hydrogel material may further comprise from 5 to 50% by weight on a dry weight basis of one or more humectants such as glycerol.

The thickness of the hydrogel layer is suitably from about 0.5 mm to about 20 mm, for example from about 1 mm to about 5 mm. As already noted, the hydrogel layer is continuous and bonded to the backing sheet around its periphery so as to for an airtight barrier between the wound and the suction aperture in the backing sheet. The hydrogel layer is therefore continuous, not permeable or semipermeable to air, and has no open area. The hydrogel layer permits the passage of liquids but not gas. The application of suction to the suction aperture therefore results in a pressure differential across the hydrogel layer that drives liquid migration through the hydrogel layer into the screen.

The area of the hydrogel layer may vary according to the type and size of wound, but is typically from about 1 $cm^2$ to about 500 $cm^2$, for example from about 4 $cm^2$ to about 100 $cm^2$.

The hydrogel layer may be separate from the screen layer. In these embodiments the hydrogel layer may be supported by the screen layer or by a separate, rigid or semi-rigid apertured support layer so that the hydrogel layer does not collapse under suction. In certain embodiments, a part or all of the hydrogel layer partially penetrates the screen layer. That is to say, the wound facing side of the screen layer is suitably impregnated with the hydrogel material. This improves fluid transfer between the hydrogel layer and the screen layer, and provides mechanical reinforcement and support to the hydrogel layer. Typically, from about 10% to about 90%, for example from about 20% to about 75%, suitably about 50% of the thickness of the screen layer may be impregnated with the hydrogel. These embodiment may be made, for example, by first impregnating the surface of the screen layer with a liquid formulation of a hydrogel prepolymer, followed by cross-linking the prepolymer in situ to form the hydrogel. For example, the hydrogel prepolymer could be a sodium alginate solution that is cross-linked in situ by treatment with a calcium salt. Alternatively, the hydrogel prepolymer could be a fluid mixture of a diisocyanate capped polyurethane prepolymer and a suitable cross-linking agent such as a primary amine that reacts in situ to form a polyurethane hydrogel. In yet other embodiments, the hydrogel prepolymer could be a solution of acrylamide monomers as described in WO-A-2004052415 that is polymerized in situ by irradiation with UV light. In yet other embodiments, the hydrogel prepolymer could be a gelatin solution that is cross-linked in situ by treatment with a cross-linking agent such as glutaraldehyde. These techniques are also useful for forming the airtight seal between the hydrogel layer and the periphery of the backing sheet.

Any of the component materials making up the screen and/or the hydrogel layer may comprise an antimicrobial material. Suitable antimicrobial agents may be selected from the group consisting of antiseptics and antibiotics and mixtures thereof. Suitable antibiotics peptide antimicrobials (e.g. defensins, Magainin, synthetic derivatives of them) tetracycline, penicillins, terramycins, erythromycin, bacitracin, neomycin, polymycin B, mupirocin, clindamycin and mixtures thereof. Suitable antiseptics include silver sulfadiazine, chlorhexidine, povidone iodine, triclosan, other silver salts and colloidal silver, sucralfate, quaternary ammonium salts and mixtures thereof. The antimicrobial agents are suitably present in the screen or the hydrogel in an amount of from about 0.001% to about 2% by weight based on the weight of the screen or the hydrogel, respectively.

Alternatively or additionally, the hydrogel may comprise one or more therapeutic agents that promote wound healing. Exemplary therapeutic agents include an antioxidant or free radical scavenger such as Vitamin C (ascorbic acid), retinoids such as Vitamin A, Vitamin E, ORC (which has been shown to have antioxidant properties), hydroquinones, benzimidazoles, antioxidant-grafted polysaccharides such as those described in U.S. Pat. No. 5,612,321, aniline or acridine dyes, or mixtures or combinations thereof. The antioxidant or free radical scavengers are suitably present in the hydrogel in an amount of from about 0.001% to about 2% by weight based on the weight of the screen or the hydrogel, respectively.

Alternatively or additionally, the hydrogel layer may contain one or more growth factors selected from the group consisting of platelet derived growth factor (PDGF), fibroblast growth factor (FGF), transforming growth factor beta (TGF-P), epidermal growth factor (EGF), vascular endothelial growth factor (VEGF) and insulin-like growth factor (IGF), and mixtures thereof. The growth factors are suitably present in the hydrogel in an amount of from about 0.0001% to about 0.1% by weight based on the weight of the screen or the hydrogel, respectively.

The wound facing surface of the dressing is suitably protected by a removable protective cover sheet. The cover sheet is typically formed from flexible thermoplastic material. Suitable materials include but are not limited to polyesters and polyolefins. Suitably, the hydrogel-facing surface of the cover sheet is a release surface. That is to say, a surface that is only weakly adherent to the hydrogel and any adhesive on the hydrogel or the backing sheet to assist peeling of the dressing from the cover sheet. For example, the cover sheet may be formed from a non-adherent plastic such as a fluoropolymer, or it may be provided with a release coating such as a silicone or fluoropolymer release coating.

Suitably, the wound dressing according to the invention is sterile and packaged in a microorganism-impermeable container.

The systems according to the present invention further comprise a source of suction in fluid communication with the aperture for applying a sub-atmospheric pressure inside the dressing in the space between the hydrogel layer and the backing sheet.

The source of suction may be an electric or manually operated air pump. It may be located remote from the dressing, or it may be attached to or form part of the dressing as in the case of micro pumps such as those described in WO-A-2007030601.

For more heavily exuding wounds it may be desirable to drain wound fluid from the dressing at least intermittently. In these embodiments the system according to the present invention suitably further comprises a wound fluid collection vessel intermediate (and in fluid communication with) the backing sheet aperture and the suction source for collecting wound fluid drained from the screen. The wound fluid collection vessel may itself form part of the suction source, for example it may be a vacuum bottle. The wound fluid collection vessel may contain an antimicrobial agent.

In the methods according to the invention, the dressings according to the invention are applied to a wound, for example an exuding wound, with the hydrogel layer covering the wound. The dressings may be secured to the intact skin around the wound by a peripheral adhesive-coated margin of the backing sheet, in conventional fashion. Alternatively or additionally the dressings may be secured in place by a suitable secondary dressing. A suction device, such as a vacuum pump or a squeeze bulb is used to withdraw air from the space between the backing sheet and the hydrogel layer, through the aperture in the backing sheet. The reduced pressure in this space may result in some compression of the screen in the said space, but the screen is sufficiently resilient to maintain its porosity and absorbency under this compression. Suitably, the screen is sufficiently resilient so that elastic recovery of the screen continues to maintain a negative pressure in the space for some time after the suction means has been withdrawn and the aperture closed. Thus, it may not be necessary to apply continuous suction to the dressing. The pressure differential across the hydrogel layer promotes migration of wound fluid through the hydrogel layer and into the absorbent screen layer. This liquid may then be drained from the screen layer and into a suitable collection vessel by continued application of suction.

The term "vacuum" or "suction" here and elsewhere in the present specification refers to any pressure below ambient atmospheric pressure. Suitably, the step of applying a vacuum includes lowering the pressure in the space between the backing sheet and the hydrogel layer to an absolute value of from about 0.1 bar to about 0.95 bar, suitably from about 0.5 bar to about 0.9 bar and typically to an absolute value of from about 0.75 bar to about 0.85 bar. The vacuum may be static or dynamic. The vacuum may be applied continuously or intermittently.

It will be appreciated that any feature or embodiment of the present invention that is described in relation to any one aspect of the invention is equally applicable to any other embodiment of the invention mutatis mutandis.

Specific embodiments of the present invention will now be discussed further, by way of example, with reference to the accompany drawings, in which:

FIG. 1 shows a perspective view of a wound dressing system according to the present invention; and FIG. 2 shows a partial longitudinal cross section through the wound dressing of the system of FIG. 1.

Referring to FIG. 1, the wound dressing system according to the invention comprises a wound dressing 1 according to the invention, a vacuum bottle 2 for providing suction, and a tube 3 connecting the vacuum bottle to the dressing. The dressing 1 comprises a flexible backing sheet 4 formed of substantially impermeable, thermoformed thermoplastic substantially in the shape of a tray having dimensions about 10 cm×10 cm×1 cm. An aperture 5 in the backing sheet 4, is connected to the tube 3. In alternative embodiments, the backing sheet may be provided with a flange around its periphery, and a layer of medically acceptable pressure-sensitive adhesive on the flange for attachment of the backing sheet to the skin around the wound being treated. The wound dressing 1 further comprises a screen 6, which in this particular embodiment is a layer of open-cellular hydrophilic polyurethane foam approximately 1 cm thick substantially filling the backing sheet. A suction manifold 8 in the form of a branched tube is embedded in the polyurethane foam and connected to the aperture 5 for efficient drainage of fluid from the foam layer. The wound facing surface of the foam layer 6 is impregnated with a continuous medically acceptable hydrogel layer 7 that extends across and bonds with the periphery of the backing sheet 4 to form an airtight seal. The hydrogel layer may, for example, be a polyurethane hydrogel or a polyacrylamide hydrogel.

The wound facing hydrogel layer in this and the other embodiments may be protected by a releasable protective sheet (not shown) prior to use. The dressing is usually packaged in a microorganism impermeable container, and is sterilised e.g. by gamma irradiation.

In use, the dressing is applied to a wound with the hydrogel layer facing and covering the wound. The vacuum bottle 2 is partially evacuated with a pump (not shown) to achieve a desired, subatmospheric pressure above the hydrogel layer. Wound fluid is drawn through the hydrogel layer and through tube 3 into bottle 2, which thereby serves also as a wound fluid collection vessel.

The above embodiment has been described for purpose of illustration. Many other embodiments falling within the scope of the accompanying claims will be apparent to the skilled reader.

The invention claimed is:

1. A system for the treatment of a tissue site with negative pressure, the system comprising:
   a source of suction; and
   a wound dressing in fluid communication with the source of suction and comprising:
      a backing sheet having an aperture for communication with the source of suction;
      a screen layer; and
      a hydrogel layer covering a wound facing side of the screen layer and bonded around a periphery to the backing sheet to form an air-impermeable hydrogel layer, wherein the hydrogel layer is resorbable.

2. The system of claim 1, wherein the screen layer is rigid or semi-rigid to support the air-impermeable hydrogel layer.

3. The system of claim 1, wherein the screen layer is a porous foam.

4. The system of claim 1, wherein the screen layer is an open-cell foam.

5. The system of claim 1, further comprising a suction manifold connected to the source of suction and located inside the screen layer.

6. The system of claim 1, wherein the hydrogel layer comprises a biopolymer.

7. The system of claim 1, wherein the hydrogel layer comprises oxidized reduced cellulose (ORC).

8. The system of claim 1, wherein the hydrogel layer comprises silver.

9. A method of treating a wound, comprising:
   applying a dressing comprising a backing sheet, a screen layer and a hydrogel layer, the hydrogel layer covering a wound facing side of the screen layer and bonded around a periphery to the backing sheet to form an air-impermeable hydrogel layer, wherein the hydrogel layer is resorbable; and
   applying reduced pressure to a non-wound-facing surface of the hydrogel layer.

10. The method of claim 9, wherein the screen layer is rigid or semi-rigid to support the air-impermeable hydrogel layer.

11. The method of claim 9, wherein the screen layer is a porous foam.

12. The method of claim 9, wherein the screen layer is an open-cell foam.

13. The method of claim 9, further comprising a suction manifold connected to the source of suction and located inside the screen layer.

14. The method of claim 9, wherein the hydrogel layer comprises a biopolymer.

15. The method of claim 9, wherein the hydrogel layer comprises oxidized reduced cellulose (ORC).

16. The method of claim 9, wherein the hydrogel layer comprises silver.

* * * * *